_(54)_ RADIATION-SENSITIVE POSITIVE RESIST COMPOSITION COMPRISING AN ALKALI SOLUBLE RESIN MADE FROM M-CRESOL, 2,3,5-TRIMETHYL PHENOL AND OPTIONALLY P-CRESOL AND A POLYPHENOL COMPOUND HAVING ALKYL OR ALKOXY SIDE GROUPS

[75] Inventors: Ayako Ida, Hyogo; Haruyoshi Osaki, Osaka; Takeshi Hioki, Osaka; Yasunori Doi, Osaka; Yasunori Uetani, Osaka; Ryotaro Hanawa, Osaka, all of Japan

[73] Assignee: Sumitomo Chemical Company, Limited, Osaka, Japan

[21] Appl. No.: 490,511

[22] Filed: Jun. 14, 1995

Related U.S. Application Data

[63] Continuation of Ser. No. 60,725, May 13, 1993, abandoned, which is a continuation of Ser. No. 569,915, Aug. 20, 1990, abandoned.

[30] Foreign Application Priority Data

| Aug. 24, 1989 | [JP] | Japan | 1-219194 |
|---|---|---|---|
| Aug. 25, 1989 | [JP] | Japan | 1-219089 |
| Sep. 8, 1989 | [JP] | Japan | 1-234380 |
| Oct. 5, 1989 | [JP] | Japan | 1-261375 |
| Oct. 6, 1989 | [JP] | Japan | 1-262712 |
| Oct. 6, 1989 | [JP] | Japan | 1-262713 |
| Dec. 27, 1989 | [JP] | Japan | 1-341457 |
| Dec. 27, 1989 | [JP] | Japan | 1-341458 |
| Dec. 27, 1989 | [JP] | Japan | 1-341459 |

[51] Int. Cl.$^6$ .................................................. G03F 7/023
[52] U.S. Cl. ........................ 430/191; 430/165; 430/192; 430/193
[58] Field of Search ................................ 430/191, 192, 430/193, 165

[56] References Cited

U.S. PATENT DOCUMENTS

| 4,626,492 | 12/1986 | Eilbeck | 430/193 |
|---|---|---|---|
| 4,731,319 | 3/1988 | Kohara et al. | 430/165 |
| 4,797,346 | 1/1989 | Yamamoto et al. | 430/165 |
| 4,812,551 | 3/1989 | Oi et al. | 430/193 |
| 4,920,028 | 4/1990 | Lazarus et al. | 430/165 |
| 4,971,887 | 11/1990 | Schmitt et al. | 430/192 |
| 5,019,479 | 5/1991 | Oka et al. | 430/193 |
| 5,153,096 | 10/1992 | Uenishi et al. | 430/192 |
| 5,215,856 | 6/1993 | Jayaraman | 430/191 |
| 5,456,995 | 10/1995 | Ozaki et al. | 430/192 |
| 5,456,996 | 10/1995 | Ozaki et al. | 430/192 |

FOREIGN PATENT DOCUMENTS

| 0239423 | 3/1987 | European Pat. Off. . |
|---|---|---|
| 0365318 | 10/1989 | European Pat. Off. . |
| 0346808 | 12/1989 | European Pat. Off. . |
| 358871 | 3/1990 | European Pat. Off. . |
| 64-090250 | 4/1989 | Japan . |
| 1189644 | 7/1989 | Japan . |

OTHER PUBLICATIONS

WPIL, No. 90-150423, Derwent Publications Ltd, London, GB.
Derwent Abstract of Jap. Pub. 1-180535 (Jul. 1989).

*Primary Examiner*—John S. Chu
*Attorney, Agent, or Firm*—Birch, Stewart, Kolasch & Birch, LLP

[57] ABSTRACT

A positive resist composition comprising 1,2-quinonediazide compound and, as an alkali-soluble resin, an alkali-soluble resin (A) which comprises a resin (I) obtainable through a condensation reaction of a mixture of m-cresol, 2,3,5-trimethylphenol and optionally p-cresol with an aldehyde and a low molecular weight novolak (II) having a weight average molecular weight of 200 to 2000 as converted to polystyrene, an alkali-soluble resin (B) which comprises a resin (I) and a compound of the general formula (III):

$$\text{HO} - \underset{(R_1)_m}{\bigcirc} - \underset{|}{\overset{R'}{\underset{|}{C}}} - \underset{(R_2)_n}{\bigcirc} - \text{OH}$$
$$\underset{(R_3)_l}{\bigcirc} \text{OH}$$

wherein $R_1$, $R_2$ and $R_3$ are respectively a $C_1$–$C_5$ alkyl group or a $C_1$–$C_5$ alkoxy group, l, m and n are respectively a number of 0 to 3, R' is a hydrogen atom or a $C_1$–$C_3$ alkyl group, or an alkali-soluble resin (C) which comprises a resin (IV) obtainable through a condensation reaction of a mixture of m-methoxyphenol and 2,3,5-trimethylphenol in a molar ratio of 80:20 to 30:70 with an aldehyde, which has good sensitivity, improved resolution and heat resistance.

1 Claim, 1 Drawing Sheet

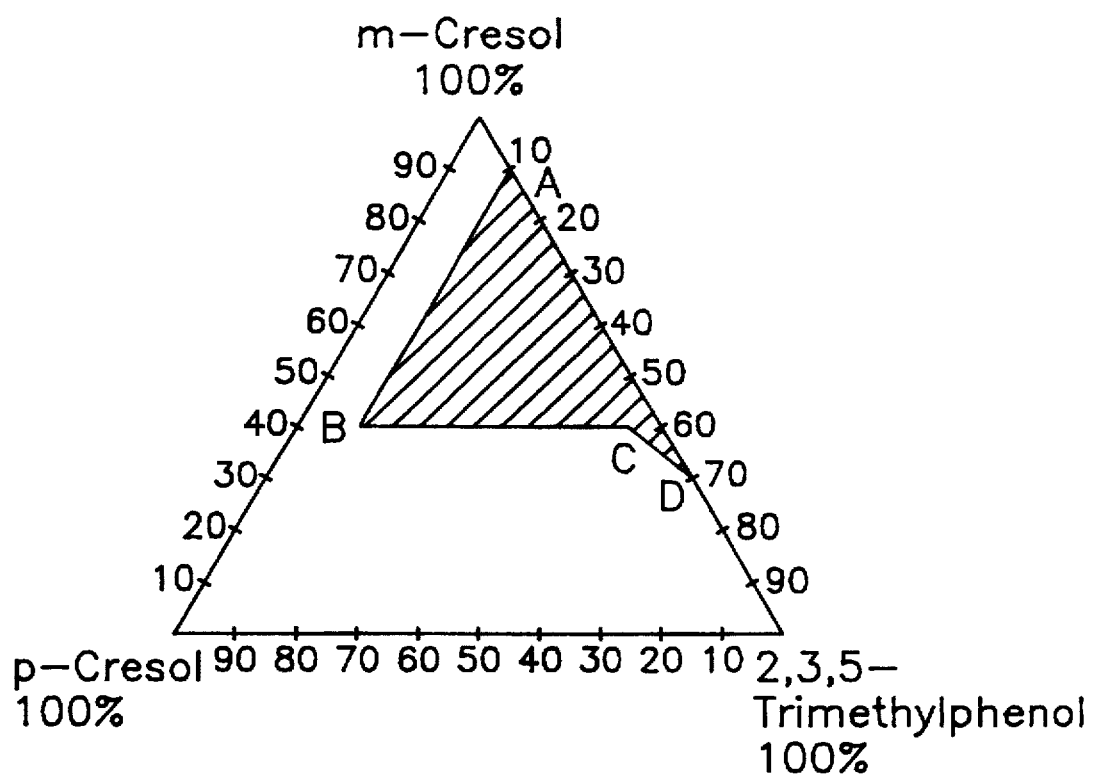

RADIATION-SENSITIVE POSITIVE RESIST COMPOSITION COMPRISING AN ALKALI SOLUBLE RESIN MADE FROM M-CRESOL, 2,3,5-TRIMETHYL PHENOL AND OPTIONALLY P-CRESOL AND A POLYPHENOL COMPOUND HAVING ALKYL OR ALKOXY SIDE GROUPS This application is a continuation of application Ser. No. 08/060,725 filed on May 13, 1993, now abandoned, which was a Rule 62 Continuation application of 07/569,915 filed Aug. 20, 1990, now abandoned.

BACKGROUND OF THE INVENTION

1. Field of the invention

The present invention relates to a radiation-sensitive resist composition which is sensitive to ultraviolet rays, far ultraviolet rays (excimer laser and so on), electron rays, ion beam and radio-active rays, e.g. x rays.

2. Description of the Related Art

Recently, particularly in the production of integrated circuits, miniaturization has proceeded as the integration level has increased, which results in demands for formation of patterns of submicron order and improved resolution. According to conventional processes for the production of integrated circuits, light exposure is accomplished by placing a mask in intimate contact to a substrate, e.g. a silicon wafer. It is said that this process cannot make patterns thinner than 2 μm. Instead of such conventional processes, the reduction projection in exposure system attracts attention. According to this new system, a pattern of a master mask (reticle) is projected on the substrate with reduction by a lens system, whereby exposure is accomplished. This system realizes a resolving power of submicron.

One of the serious problems in this system is low throughput. Namely, in this system, the total exposure time to expose a wafer is very long because of divided and repeated light exposure unlike a batch light exposure system which is employed in conventional mask contact printing methods.

To solve this problem, not only an improvement in the apparatus but also an increase in sensitivity of the resist to be used are important. If the exposure time can be shortened by an increase in the sensitivity, the throughput and in turn the yield can be improved.

On the other hand, as the distance between the two adjacent lines is decreased with an increase in the integration level, dry etching is predominantly used rather than wet etching. The photoresist should have better heat resistance than ever.

When the positive photoresist now in practical use is checked from this standpoint, its sensitivity, resolving power and heat resistance are not necessarily satisfactory. Generally, the positive photoresist has lower sensitivity than the negative photoresist and improvement in the sensitivity of the former is desired.

To increase the sensitivity, it is easiest to decrease a molecular weight of a novolak resin used in the positive photoresist. The decrease of the novolak resin molecular weight accelerates dissolution of the photoresist in an alkaline developer so that the apparent sensitivity of the photoresist is increased.

This method, however, has a very serious disadvantage that the heat resistance of the photoresist deteriorates. Moreover, it encounters some problems, e.g. large film thickness loss in an unexposed area (reduction of so-called film thickness retention), worsening a shape of the pattern, deterioration of the γ-value because of small differences in the dissolving rates in the developing solution between the exposed area and the unexposed area.

In view of this, positive resists satisfying sensitivity, resolving power and heat resistance at the same time have not been on the market up to now. Attempts to improve one of these three characteristics leave at least one of the remaining characteristics impaired.

SUMMARY OF THE INVENTION

One object of the present invention is to provide a positive resist composition which can overcome the above problems associated with conventional positive resist compositions.

According to a first aspect of the present invention, there is provided a positive resist composition comprising 1,2-quinonediazide compound and an alkali-soluble resin (A) which comprises a resin (I) obtainable through a condensation reaction of a mixture of m-cresol, 2,3,5-trimethylphenol and optionally p-cresol with an aldehyde and a low molecular weight novolak (II) having a weight average molecular weight of 200 to 2000 as converted to polystyrene.

According to a second aspect of the present invention, there is provided a positive resist composition comprising 1,2-quinonediazide compound and an alkali-soluble resin (B) which comprises a resin (I) obtainable through a condensation reaction of a mixture of m-cresol, 2,3,5-trimethylphenol and optionally p-cresol with an aldehyde and a compound of the general formula (III):

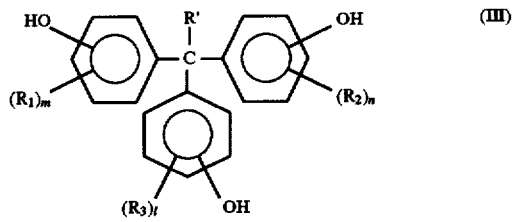

wherein $R_1$, $R_2$ and $R_3$ are respectively a $C_1$–$C_5$ alkyl group or a $C_1$–$C_5$ alkoxy group, l, m and n are respectively a number of 0 to 3, R' is a hydrogen atom or a $C_1$–$C_3$ alkyl group.

According to a third aspect of the present invention, there is provided a positive resist composition comprising 1,2-quinonediazide compound and an alkali-soluble resin (C) which comprises a resin (IV) obtainable through a condensation reaction of a mixture of m-methoxyphenol and 2,3,5-trimethylphenol in a molar ratio of 80:20 to 30:70 with an aldehyde.

BRIEF DESCRIPTION OF THE DRAWINGS

FIGURE is a ternary diagram indicating a preferred molar ratio among m-cresol, p-cresol and 2,3,5-trimethylphenol for the preparation of the resin (I).

DETAILED DESCRIPTION OF THE INVENTION

The resin (I) is prepared through a condensation reaction of m-cresol, 2,3,5-trimethylphenol and optionally p-cresol with an aldehyde in the presence of an acid catalyst. This condensation reaction is carried out at a temperature of from 60° to 120° C. for 2 to 30 hours.

Examples of the aldehyde are formaldehyde paraformaldehyde, acetaldehyde, propylaldehyde, benzaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, glutaraldehyde, glyoxal, o-methylbenzaldehyde, p-methylbenzaldehyde and so on. They may be used alone or in combination. In particular, formaldehyde which is commercially mass produced is suitably used.

As the acid catalyst, any of the conventionally used ones such as organic acids, inorganic acid or divalent metal salts can be used. Specific examples of the acid catalyst are oxalic acid, hydrochloric acid, sulfuric acid, perchloric acid, p-toluenesulfonic acid, trichloroacetic acid, phosphoric acid, formic acid, zinc acetate, manganese acetate, etc.

The condensation reaction may be carried out in the presence or absence of a solvent. When the solvent is used, ethylcellosolve acetate is preferably used, since ethylcellosolve acetate can be used as a resist solvent and the photoresist composition exhibits improved heat resistance.

As a ratio of 2,3,5-trimethylphenol contained in the mixture is larger, the heat resistance of the photoresist composition is more improved. However, because of balance between the sensitivity and resoluion, a molar ratio of m-cresol, p-cresol and 2,3,5-trimethylphenol is preferably selected from a hatched area (including the border lines) in a ternary diagram of FIGURE. The hatched area is defined by four vertexes A, B, C and D:

| A: | m-cresol | 90% by mole |
|---|---|---|
|  | p-cresol | 0% by mole |
|  | 2,3,5-trimethylphenol | 10% by mole |
| B: | m-cresol | 40% by mole |
|  | p-cresol | 50% by mole |
|  | 2,3,5-trimethylphenol | 10% by mole |
| C: | m-cresol | 40% by mole |
|  | p-cresol | 5% by mole |
|  | 2,3,5-trimethylphenol | 55% by mole |
| D: | m-cresol | 30% by mole |
|  | p-cresol | 0% by mole |
|  | 2,3,5-trimethylphenol | 70% by mole |

Preferably, the novolak resin (I) which is characterized in the following area ratio in a gel permeation chromatographic pattern (GPC pattern) measured by using a UV light (254 nm) detector is used:

An area ratio of a range in which the molecular weight as converted to polystyrene is not larger than 900 dose not exceed 25%, more preferably, an area ration of a range in which the molecular weight as converted to polystyrene is not larger than 6000 is from 40% to 65%, especially from 50 to 65%. This is because, under such conditions, the heat resistance is much improved and a developing residue is hardly produced.

The novolak resin characterized as above is obtained through crystallization, fractionation, etc. For example, a synthesized novolak resin is dissolved in a good solvent, and water is poured in a resulting solution to precipitate the novolak resin. Alternatively, a synthesized novolak resin is poured in heptane, hexane, pentane, cyclohexane and the like to fractionate it.

Examples of the good solvent are alcohols (e.g. methanol, ethanol, etc.), ketones (e.g. acetone, methyl ethyl ketone, methyl isobutyl ketone, etc.), ethylene glycol and its ethers or ether esters (e.g. ethylcellosolve, ethylcellosolve acetate, etc.), tetrahydrofuran and so on.

Moreover, the resin (I) which is obtained by the above method and has a weight average molecular weight of 2000 to 20,000 as converted to polystyrene is more preferably used.

The low molecular weight novolak (II) is prepared through a condensation reaction of a phenol compound with an aldehyde in the presence of an acid catalyst.

Examples of the phenol compound which is condensed with the aldehyde include phenol, o-cresol, m-cresol, p-cresol, 3,5-xylenol, 2,5-xylenol, 2,3-xylenol, 2,4-xylenol, 2,6-xylenol, 3,4-xylenol, 2,3,5-trimethylphenol, resorcinol and so on. Among them, cresol isomers are preferably used.

These phenol compounds may be used alone or in combination by taking their solubility in an alkaline developing solution into consideration.

Examples of the aldehyde is formaldehyde, paraformaldehyde, acetaldehyde, glyoxal and so on. In particular, 37% formalin which is commercially mass produced is suitably used.

As the acid catalyst, those as exemplified in the above may be used.

This condensation reaction is carried out at a temperature of 30° to 250° C. for 2 to 30 hours.

The reaction may be carried out in the presence or absence of a solvent.

The low molecular weight novolak (II) has a weight average molecular weight of 200 to 2000, more preferably 200 to 1000, as converted to polystyrene. When the low molecular weight novolak (II) has the weight average molecular weight of 200 to 2000 as converted to polystyrene, the photoresist composition exhibits excellent sensitivity, adhesion to a substrate and heat resistance.

The molecular weight of the low molecular weight novolak (II) is easily controlled through control of a molar ratio of the aldehyde to the phenol compound.

To prepare the novolak resin having the weight average molecular weight of 200 to 2000 as converted to polystyrene in case of m-cresol-formaldehyde resin, a molar ratio of m-cresol to formaldehyde in the condensation reaction is preferably from 0.65 to 0.05.

Preferably, unreacted monomers are removed through distillation.

As the compounds (III), the following compounds are preferably used:

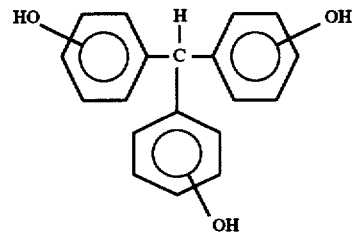

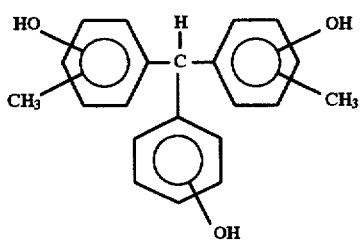

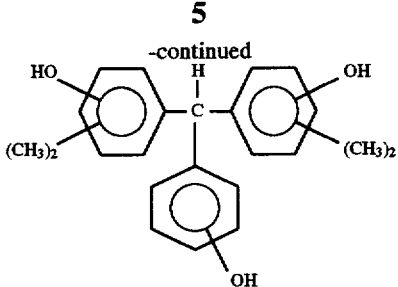

more preferably,

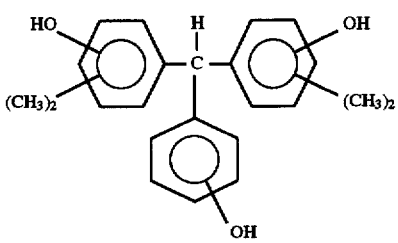

Most preferred compounds are

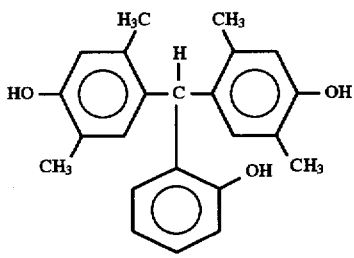

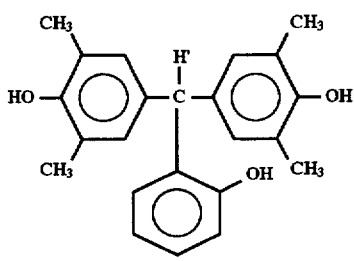

The compound (III) can be prepared by a condensation reaction of a phenol compound with a carbonyl compound in the presence of an acid catalyst.

Examples of the phenol compound which is condensed with the carbonyl compound include phenol, o-cresol, m-cresol, p-cresol, 3,5-xylenol, 2,5-xylenol, 2,3-xylenol, 2,4-xylenol, 2,6-xylenol, 3,4-xylenol, 2,3,5-trimethylphenol, 4-tert.-butylphenol, 2,-tert.-butylphenol, 3-tert.-butylphenol, 4-methoxyphenol, 3-methoxyphenol, 2-methoxyphenol, 2,3-dimethoxyphenol, 2,5-dimethoxyphenol, 3,5-dimethoxyphenol, 3-ethylphenol, 2-ethylphenol, 4-ethylphenol, 2,3,5-triethylphenol, 3,5-diethylphenol, 2,5-diethylphenol, 2,3-diethylphenol and so on.

These phenol compounds may be used alone or in combination.

Examples of the carbonyl compound include benzaldehyde, o-hydroxybenzaldehyde, m-hydroxybenzaldehyde, p-hydroxybenzaldehyde, o-hydroxyacetophenone, m-hydroxyacetophenone, p-hydroxyacetophenone, 3-methoxy-4-hydroxybenzaldehyde and so on.

These carbonyl compounds may be used alone or in combination.

Examples of the acid catalyst to be used in this condensation reaction include organic acids or inorganic acids (e.g. oxalic acid, formic acid, p-toluenesulfonic acid, trichloroacetic acid, hydrochloric acid, sulfuric acid, perchloric acid, phosphoric acid, etc.), salts of divalent metals (e.g. zinc acetate, zinc chloride, magnesium acetate, etc.) and so on.

The amount of the carbonyl compound to be used in the condensation reaction is from 0.02 to 3 moles per mole of the phenol compound. The amount of the acid catalyst to be used in the condensation reaction is from 0.01 to 0.7 mole per mole of the carbonyl compound.

This condensation reaction may be carried out at a temperature of 30° to 250° C. for 2 to 30 hours.

The reaction may be carried out in the presence or absence of a solvent.

Suitable solvents include water, alcohols (e.g. methanol, ethanol, isopropanol, n-butanol, isoamyl alcohol, etc.), ethylcellosolve acetate, ethylcellosolve, methylcellosolve, methyl isobutyl ketone, methyl ethyl ketone, hexane, cyclohexane, heptane, benzene, toluene, xylene and so on.

Preferably, the amount of the solvent is from 10 to 500 parts by weight per 100 parts by weight of the total weight of phenol compound and the carbonyl compound.

After removing the metal ions, the condensation product can be purified by a suitable method such as recrystallization and reprecipitation.

One method for the removal of the metal ions is as follow:

The product is dissolved in an organic solvent which can be separated from a mixture with water, and washed with ion-exchanged water. Examples of such organic solvent include methyl isobutyl ketone, ethylcellosolve acetate, ethyl acetate and so on.

Another method for the removal of the metal ions is as follow:

The product is dissolved in an organic solvent which is not separated from a mixture with water, and charged into ion-exchanged water to precipitate the product. Examples of such organic solvent include methanol, ethanol, acetone and so on. This method is preferred, because the removal of the metal ions and purification of the condensation product are done at the same time.

Additional alkali-soluble resin other than the resin (I) and the low molecular weight novolak (II) can be added to the alkali-soluble resin (A) insofar as the effects of the present invention are achieved.

Additional alkali-soluble resin other than the resin (I) and the compound (III) can be added to the alkali-soluble resin (B) insofar as the effects of the present invention are achieved.

Examples of the other alkali-soluble resins are polyvinylphenol, a novolak resin and so on. The novolak resin is prepared by an addition condensation reaction of a phenol compound with formaldehyde. Specific examples of the phenol compound used as one of the raw materials for the synthesis of the novolak resin include phenol, o-cresol, m-cresol, p-cresol, 2,5-xylenol, 3,5-xylenol, 3,4-xylenol, 2,3,5-trimethylphenol, 4-tert.-butylphenol, 2-tert.-butylphenol, 3-tert.-butylphenol, 3-ethylphenol, 2-ethylphenol, 4-ethylphenol, 2-naphthol, 1,3-dihydroxynaphthalene, 1,7-dihydroxynaphthalene, 1,5-dihydroxynaphthalene, etc. These phenols may be used alone or in combination.

The amount of the low molecular weight novolak (II) is from 4 to 50 parts by weight per 100 parts by weight of the alkali-soluble resin (A). When the amount of the low molecular weight novolak (II) is in this range, it is easy to develop and make pattern.

The amount of the compound (III) is from 4 to 40 parts by weight per 100 parts by weight of the alkali-soluble resin (B). When the amount of the compound (III) is in this range, it is easy to develop and make the pattern.

The novolak (IV) is prepared through a condensation reaction of m-methoxyphenol and 2,3,5-trimethylphenol with an aldehyde in the presence of an acid catalyst.

The condensation reaction may be carried out at a temperature of 60° to 120° C. for 2 to 30 hours.

Examples of the aldehyde are formaldehyde, paraformaldehyde, acetaldehyde, propylaldehyde, benzaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, glutaraldehyde, glyoxal, o-methylbenzaldehyde, p-methylbenzaldehyde and so on. In particular, formaldehyde which is commercially mass produced is suitably used.

Examples of the acid catalyst to be used in this condensation reaction includes organic or inorganic acids (e.g. oxalic acid, formic acid, p-toluenesulfonic acid, trichloroacetic acid, hydrochloric acid, sulfuric acid, perchloric acid, phosphoric acid, etc.), salts of divalent metals (e.g. zinc acetate, magnesium acetate, etc.) and so on.

The reaction may be carried out in the presence or absence of a solvent.

The molar ratio of m-methoxyphenol to 2,3,5-trimethylphenol is preferably from 80:20 to 30:70.

When the molar ratio of m-methoxyphenol exceeds 80%, it is difficult to make the pattern because unirradiated parts are easily dissolved in the developer.

When the molar ratio of m-methoxyphenol is less than 30%, it is difficult to develop the photoresist composition because of decrease in solubility in the developer.

The resin (IV) having the weight average molecular weigh of from 2000 to 20,000, in particular, from 4000 to 15,000 is preferably used.

The photoresist composition contains the alkali-soluble resin (C) which comprises the resin (IV) and the compound (III), particularly the resin (IV) which is characterized in that an area ratio of a range in which the molecular weight as converted to polystyrene is not larger than 900 is not more than 15%. Preferably, the compound (III) is used in an amount of 4 to 40 parts by weight per 100 parts by weight of the total weight of the alkali-soluble resin (C). When the amount of the compound (III) is in this range, it is easy to make the pattern.

The resin having the above characteristic is prepared through a conventional condensation reaction and the above described post-treatment such as fractionation and the like.

Additional alkali-soluble resin other than the resin (IV) and the low molecular weight novolak (II) can be added to the alkali-soluble resin (C) insofar as the effects of the present invention are achieved.

Examples of the other alkali-soluble resins are polyvinylphenol, a novolak resin and so on. The novolak resin is prepared by an addition condensation reaction of a phenol compound with formaldehyde. Specific examples of the phenol compound used as one of the raw materials for the synthesis of the novolak resin include phenol, o-cresol, m-cresol, p-cresol, 2,5-xylenol, 3,5-xylenol, 3,4-xylenol, 2,3,5-trimethylphenol, 4-tert.-butylphenol, 2-tert.-butylphenol, 3-tert.-butylphenol, 3-ethylphenol, 2-ethylphenol, 4-ethylphenol, 2-naphthol, 1,3-dihydroxynaphthalene, 1,7-dihydroxynaphthalene, 1,5-dihydroxynaphthalene, etc. These phenols may be used alone or in combination.

The 1,2-quinone diazide compound to be used as a sensitizer in the positive resist composition of the present invention is not limited. Specific examples of the 1,2-quinone diazide compound are 1,2-benzoquinone diazide-4-sulfonic acid ester, 1,2-naphthoquinone diazide-4-sulfonic acid ester, 1,2-naphthoquinone diazide-5-sulfonic acid ester, etc.

Above esters may be prepared by per se conventional methods. For example, the ester is prepared by a condensation reaction of a compound having a hydroxyl group with 1,2-naphthoquinone diazide sulfonyl chloride or benzoquinone diazide sulfonyl chloride in the presence of a weak alkali.

Examples of the compound having a hydroxyl group are hydroquinone, resorcinol, phloroglucin, 2,4-dihydroxybenzophenone, 2,3,4-trihydroxybenzophenone, 2,3,4,4'-tetrahydroxybenzophenone, 2,2',4,4'-tetrahydroxybenzophenone, bis(p-hydroxyphenyl)methane, bis(2,4-dihydroxyphenyl)methane, bis(2,3,4-trihydroxyphenyl)methane, 2,2-bis(p-hydroxyphenyl) propane, 2,2-bis(2,4-dihydroxyphenyl)propane, 2,2-bis(2,3,4-trihydroxyphenyl)-propane, hydroxyflavan compounds and the like. Among them, ester of 2,3,4,4'-tetrahydroxybenzophenone (at least two hydroxy groups on the average are esterified) or hydroxyflavan compounds (at least two hydroxy groups on the average are esterified) of the formula:

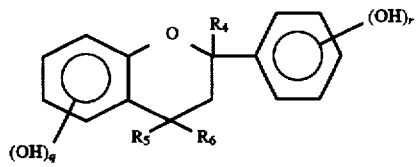

wherein q is a number of 0 to 4, r is a number of 1 to 5, $R_4$, $R_5$ and $R_6$ are respectively a hydrogen atom, an alkyl group, an alkenyl group, a cyclohexyl group or an aryl group, with 1,2-naphthoquinonediazide-5-sulfonic acid are preferably used as 1,2-quinonediazide compounds.

The positive resist composition of the present invention may contain two or more 1,2-quinonediazide compounds in combination.

The positive resist composition is prepared by mixing and dissolving the 1,2-quinonediazide compound and the alkali-soluble resin in a solvent.

The amount of the 1,2-quinonediazide compound is 5 to 100, preferably 10 to 50 parts by weight per 100 parts by weight of the alkali-soluble resin.

When the amount of the 1,2-quinonediazide compound is less than 5 parts by weight, it is difficult to make the pattern because the composition easily dissolves in the developer. When the amount of the 1,2-quinonediazide compound exceeds 100 parts by weight, the irradiation cannot decompose all the 1,2-quinonediazide compound added. A large irradiation dose will deteriorate the sensitivity.

Preferably, the used solvent evaporates at a suitable drying grate to give a uniform and smooth coating film. Such a solvent includes ethylcellosolve acetate, methylcellosolve acetate, ethylcellosolve, methylcellosolve, propyleneglycol monomethyl ether acetate, butyl acetate, methyl isobutyl ketone, xylene, etc.

To the positive photoresist composition obtained by the foregoing method, small amounts of resins, dyes, etc. may be added if desired.

The resist composition of the present invention has better sensitivity and also improved resolution and heat resistance in comparison with the conventional ones.

PREFERRED EMBODIMENTS OF THE INVENTION

The present invention will be illustrated more in detail with the following Examples, but it is not limited to these Examples. In Examples, "parts" are by weight unless otherwise indicated.

The definitions of the terms used in Examples are as follows:

Sensitizer (1)

A condensation product of naphthoquinone-(1,2)-diazide-(2)-5-sulfonyl chloride with

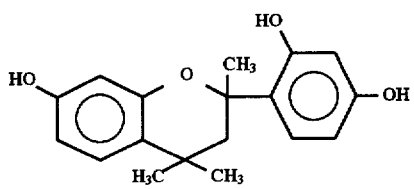

(2.6 Hydroxy groups on the average are esterified.)

Sensitizer (2)

A condensation product of naphthoquinone-(1,2)-diazide-(2)-5-sulfonyl chloride with 2,3,4,4'-tetrahydroxybenzophenone. (2.5 Hydroxy groups on the average are esterified.)

Heat resistance

A temperature in a clean oven at which the resist pattern begins to soften and flow.

Adhesion

Adhesion to a SOG substrate. (O ... good, Δ ... possible, X ... impossible)

Area ratio I

An area ratio (%) of a pattern area of the gel permeation chromatographic pattern (GPC pattern) [measured by the use of a UV (254 nm) detector] of a range wherein the molecular weight as converted to polystyrene is not larger than 6000 to the whole GPC pattern area.

Area ratio II

An area ratio (%) of a pattern area of the gel permeation chromatographic pattern (GPC pattern) [measured by the use of a UV (254 nm) detector] of a range wherein the molecular weight as converted to polystyrene is not larger than 900 to the whole GPC pattern area.

SYNTHETIC EXAMPLE 1

Into a three-necked 1000 ml flask, m-cresol (189.2 g), 2,3,5-trimethylphenol (102.2 g) (m-cresol/2,3,5-trimethylphenol=70/30 (in molar ratio)), ethylcellosolve acetate (252 g) and a 5% aqueous solution of oxalic acid (30.4 g) were added. Then, to the mixture, a 37.0% formalin (186.5 g) was dropwise added over 40 minutes while heating and stirring under reflux. Thereafter, the reaction mixture was heated while stirring for further 14 hours. After neutralization, washing with water and removing water, a solution of a novolak resin in ethylcellosolve acetate was obtained.

The weight average molecular weight was measured by GPC. The result is shown in the Table 1.

SYNTHETIC EXAMPLE 2

Into a three-necked 1000 ml flask, m-cresol (189.2 g), 2,3,5-trimethylphenol (102.2 g) (m-cresol/2,3,5-trimethylphenol=70/30 (in molar ratio)), ethylcellosolve acetate (252 g) and a 5% aqueous solution of oxalic acid (30.4 g) were added. Then, to the mixture, a 37.0% formalin (186.5 g) was dropwise added over 40 minutes while heating and stirring under reflux. Thereafter, the reaction mixture was heated while stirring for further 9 hours. After neutralization, washing with water and removing water, a solution of a novolak resin in ethylcellosolve acetate was obtained.

The weight average molecular weight was measured by GPC. The result is shown in the Table 1.

SYNTHETIC EXAMPLE 3

Into a three-necked 1000 ml flask, m-cresol (175.7 g), 2,3,5-trimethylphenol (119.0 g) (m-cresol/2,3,5-trimethylphenol=65/35 (in molar ratio)), ethylcellosolve acetate (252 g) and a 5% aqueous solution of oxalic acid (30.4 g) were added. Then, to the mixture, a 37.0% formalin (188.5 g) was dropwise added over 40 minutes while heating and stirring under reflux. Thereafter, the reaction mixture was heated while stirring for a further 14 hours. After neutralization, washing with water and removing water, a solution of a novolak resin in ethylcellosolve acetate was obtained.

The weight average molecular weight was measured by GPC. The result is shown in the Table 1.

SYNTHETIC EXAMPLES 4–9

In the same procedure as in Synthetic Example 1, resins in Table 1 were obtained.

TABLE 1

| Synthetic Example No. | Molar ratio m-cresol/ 2,3,5-trimethyl-phenol | The weight average molecular weight converted to polystyrene Mw | The area ratio I | The area ratio II |
|---|---|---|---|---|
| 1 | 70/30 | 6300 | 71 | 32 |
| 2 | 70/30 | 4800 | | 32 |
| 3 | 65/35 | 5800 | 72 | 24 |
| 4 | 70/30 | 6300 | | 28 |
| 5 | 60/40 | 4800 | | 28 |
| 6 | 80/20 | 5300 | | 24 |
| 7 | 80/20 | 6000 | | 25 |
| 8 | 80/20 | 8300 | | 25 |
| 9 | 65/35 | 4500 | | 23 |

SYNTHETIC EXAMPLE 10

The solution of novolak resin in ethylcellosolve acetate obtained in Synthetic Example 1 (the content of the novolak resin, 42%) (200 g) was added to a 3 liter separable flask, and then ethylcellosolve acetate (360 g) and n-heptane (276 g) were added. After stirring for 30 minutes at 20° C., the resulting mixture was left standing and separated. n-Heptane in the recovered lower layer was removed by an evaporator to obtain a novolak resin in ethylcellosolve acetate.

The weight average molecular weight was measured by GPC. The result is shown in the Table 2.

SYNTHETIC EXAMPLE 11

The solution of novolak resin in ethylcellosolve acetate obtained in Synthetic Example 2 (the content of the novolak resin, 35.0%) (200 g) was added to a 3 liter separable flask, and then ethylcellosolve acetate (733.3 g) and n-heptane (706.4 g) were added. After stirring for 30 minutes at 20° C., the resulting mixture was left standing and separated. n-Heptane in the recovered lower layer was removed by an evaporator to obtain a novolak resin in ethylcellosolve acetate.

The weight average molecular weight was measured by GPC. The result is shown in the Table 2.

SYNTHETIC EXAMPLE 12

The same procedures as in Synthetic Example 10 were repeated except that the solution of novolak resin in ethylcellosolve acetate obtained in Synthetic Example 3 (the content of the novolak resin, 40%) was used to obtain a novolak resin in ethylcellosolve acetate.

The weight average molecular weight was measured by GPC. The result is shown in the Table 2.

SYNTHETIC EXAMPLES 13-22

The same procedures as in Synthetic Example 11 were repeated except that the ethylcellosolve acetate solution of novolak resin in Table 2 was used or the amount of ethylcellosolve acetate solution was changed.

TABLE 2

| Synthetic Example No. | Kind of used resin Synthetic Example No. | The weight average molecular weight converted to polystyrene Mw | The area ratio I | The area ratio II |
|---|---|---|---|---|
| 10 | 1 | 9300 | 54 | 20 |
| 11 | 2 | 8200 |  | 12.9 |
| 12 | 3 | 8800 | 52 | 11.2 |
| 13 | 2 | 7800 |  | 17.5 |
| 14 | 4 | 9900 |  | 12.8 |
| 15 | 4 | 9400 |  | 18.0 |
| 16 | 4 | 8300 |  | 20.0 |
| 17 | 6 | 9900 |  | 12.5 |
| 18 | 7 | 9500 |  | 4.3 |
| 19 | 8 | 12300 |  | 0.8 |
| 20 | 8 | 9700 |  | 7.1 |
| 21 | 9 | 7000 |  | 16.6 |
| 22 | 11 | 8800 |  | 11.2 |

SYNTHETIC EXAMPLE 23

In a 1000 ml three-necked flask, were added m-cresol (149 g), p-cresol (121 g), ethylcellosolve acetate (252 g) and a 5% aqueous solution of oxalic acid (30.4 g). Then, to the mixture, a 37.0% formalin (147.8 g) was dropwise added over 40 minutes while heating and stirring on under reflux. Thereafter, the reaction mixture was heated while stirring for further 7 hours. After neutralization, washing with water and removing water, a solution of a novolak resin in ethylcellosolve acetate was obtained.

The weight average molecular weight measured by GPC was 9600 as converted to polystyrene.

SYNTHETIC EXAMPLE 24

The solution of novolak resin in ethylcellosolve acetate obtained in Synthetic Example 23 (the content of the novolak resin, 41.2%) (120 g) was charged in a 3 liter separable flask, and then ethylcellosolve acetate (868.8 g) and n-heptane (544.6 g) were added. After stirring for 30 minutes at 20° C., the resulting mixture was left standing and separated. n-Heptane in the recovered lower layer was removed by an evaporator to obtain a novolak resin in ethylcellosolve acetate.

The weight average molecular weight measured by GPC was 15500 as converted to polystyrene. The area ratio II was 7%.

SYNTHETIC EXAMPLE 25

Into a three-necked 1000 ml flask, m-cresol (270 g) and a 1% aqueous solution of oxalic acid (48.7 g) were added. Then, to the mixture, a 37.0% aqueous solution of formalin (60.8 g) was dropwise added over 40 minutes while heating and stirring under reflux. Thereafter, the reaction mixture was heated while stirring for further 2 hours. After neutralization, washing with water and removing water, a solution of a novolak resin in ethylcellosolve acetate was obtained, which is referred as the novolak A.

The weight average molecular weight measured by GPC was 330.

SYNTHETIC EXAMPLE 26

Into a 500 ml flask equipped with a stirrer, a condenser, a water separator and a thermometer, 2,5-xylenol (134.0 g), salicylaldehyde (33.7 g), p-toluenesulfonic acid (0.83 g) and toluene (268 g) were added and stirred on an oil bath at 115° C. for 16 hours while removing condensed water. The resulting mixture was filtered at a temperature of 50° to 60° C. to obtain a crude cake.

The crude cake was dissolved in methanol (580 g) at a temperature of 20° to 25° C. and charged into ion-exchanged water (1450 g). Thereafter, the resulting solution was filtered and dried to obtain the compound (a) of the formula (a) (89.3 g). Yield, 98.0% (based of salicylaldehyde).

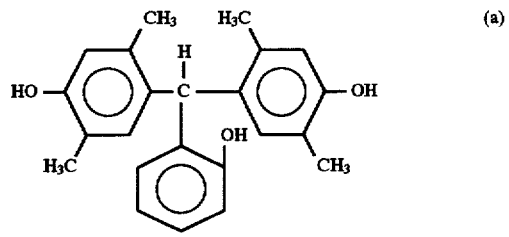

MS: m/e=348 (M$^+$)

NMR in acetone-d$_6$ (standard: TMS): δ(ppm)=2.04 (s, 12H), 5.85 (s, 1H), 6.52 (s, 2H), 6.63 (s, 2H), 6.74 (m, 2H), 6.83 (d, 1H), 7.05 (m, 1H), 7.78 (s, 1H), 8.09 (s, 1H)

Melting point: 274°-275° C.

EXAMPLES 1-12

Each of the novolak A obtained in Synthetic Example 25, the compound (a) obtained in Synthetic Example 26 and the novolak resins obtained in Synthetic Examples 1-24 was dissolved together with a sensitizer in ethylcellosolve acetate in amounts in Table 3 to prepare a resist solution. The amount of the solvent was adjusted to form a film having a thickness of 1.28 μm when the resist solution was applied under the coating conditions below.

Each composition was filtered through a Teflon (trade mark) filter of 0.2 μm in pore size to prepare a resist solution. The solution was then coated on a silicon wafer, which had been rinsed in a usual manner, by means of a spinner at 4000 rpm. The coated silicon wafer was baked for one minute on a vacuum adsorption-type hot plate kept at 100° C. and exposed to light the exposure time of which was varied stepwise at each shot by means of a reduction projection exposure apparatus with an extra-high pressure mercury lamp as a light source. Thereafter, the silicon wafer was developed in a developer (SOPD (trade name) manufactured by Sumitomo Chemical Company, Limited) to obtain a positive pattern. After rinsing and drying, the amount of film thickness loss for each shot was plotted against the exposure time to calculate sensitivity. The film thickness retention was calculated from the remaining film thickness in the unexposed area. Also, the silicon wafer having a resist pattern was placed for 30 minutes in a clean oven set at various temperatures in the air, and the heat resistance was evaluated by observing the resist pattern by means of a scanning electron microscope.

COMPARATIVE EXAMPLES 1–4

The same procedures as in Example 1 were repeated, except that the novolak A and the compound (a) were not added to prepare a resist composition.

In the same method as in Example 1, the sensitivity and the film thickness retention were calculated and the heat resistance was evaluated.

These results are collectively shown in Table 3.

It is seen from the results in Table 3 that balance between the sensitivity and heat resistance in the Examples is markedly improved in comparison with Comparative Examples.

TABLE 4

| Synthetic Example No. | Molar ratio m-cresol/p-cresol 2,3,5-trimethylphenol | The weight average molecular weight converted as polystyrene Mw | The area ratio II |
|---|---|---|---|
| 27 | 70/20/10 | 4180 | 38 |
| 28 | 70/20/10 | 5560 | 35 |
| 29 | 70/20/10 | 6280 | 35 |
| 30 | 70/10/20 | 3300 | 36 |
| 31 | 70/10/20 | 4290 | 36 |
| 32 | 70/10/20 | 5540 | 35 |
| 33 | 60/20/20 | 4060 | 37 |
| 34 | 60/20/20 | 4500 | 36 |
| 35 | 60/20/20 | 5930 | 35 |
| 36 | 70/10/20 | 12350 | 32 |

TABLE 3

| | Example No. | | | | | | | | | | | | Comp. Ex. No. | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 1 | 2 | 3 | 4 |
| Amount of the compound (a) (parts) | — | — | 3.5 | 4.0 | 3.5 | 3.0 | 4.0 | 4.0 | 4.0 | 3.5 | 3.5 | 3.5 | — | — | — | — |
| Amount of novolak A (parts) | 3.5 | 3.5 | — | — | — | — | — | — | — | — | — | — | — | — | — | — |
| Amount of novolak resin (parts) | 13.5 | 13.5 | 13.5 | 13.0 | 13.5 | 14.0 | 13.0 | 13.0 | 13.0 | 13.5 | 13.5 | 13.5 | 17.0 | 17.0 | 17.0 | 17.0 |
| Kind of cresol novolak resin (Synthetic Example No.) | 10 | 12 | 13 | 14 | 15 | 16 | 17 | 18 | 19 | 20 | 21 | 22 | 14 | 23 | 5 | 24 |
| Sensitizer: | | | | | | | | | | | | | | | | |
| Kind | (1) | (2) | (1) | (1) | (1) | (1) | (1) | (1) | (1) | (1) | (1) | (2) | (1) | (2) | (1) | (2) |
| Amount (parts) | 4.0 | 4.5 | 4.0 | 4.0 | 4.0 | 4.0 | 4.0 | 4.0 | 4.0 | 4.0 | 4.0 | 4.5 | 4.0 | 4.5 | 4.0 | 4 |
| Sensitivity (msec) | 394 | 166 | 215 | 277 | 262 | 232 | 190 | 180 | 247 | 179 | 274 | 151 | 970 | 85 | 261 | 980 |
| Film thickness retention (%) | 100 | 99.2 | 99.5 | 99.7 | 99.6 | 99.5 | 99.6 | 99.8 | 100 | 99.6 | 100 | 98.5 | 99.9 | 98.4 | 99.8 | 100 |
| Heat resistance (°C.) | 165 | 160 | 160 | 160 | 160 | 155 | 150 | 155 | 165 | 160 | 160 | 160 | 150 | 140 | 145 | 150 |
| Resolution (μm) | 0.55 | 0.55 | 0.5 | 0.50 | 0.55 | 0.55 | 0.6 | 0.55 | 0.5 | 0.55 | 0.55 | 0.55 | 1.0 | 0.9 | 0.7 | 1.0 |
| Adhesion | ○ | ○ | | | | | | | | | | | | | | |

SYNTHETIC EXAMPLE 27

Into a three-necked 1000 ml flask, m-cresol (189 g), p-cresol (54 g), 2,3,5-trimethylphenol (34 g), ethylcellosolve acetate (252 g) and a 5% aqueous solution of oxalic acid (30.4 g) were added. Then, to the mixture, a 37.0% formalin (152 g) was dropwise added over 40 minutes while heating and stirring under reflux. Thereafter, the reaction mixture was heated while stirring for further 7 hours. After neutralization, washing with water and removing water, a solution of a novolak resin in ethylcellosolve acetate was obtained.

The weight average molecular weight was measured by GPC. The result is shown in the Table 4.

SYNTHETIC EXAMPLES 28–36

The same procedures as in Synthetic Example 27 were repeated to obtain resins shown in Table 4.

SYNTHETIC EXAMPLE 37

The solution of novolak resin in ethylcellosolve acetate obtained in Synthetic Example 27 (the content of the novolak resin, 40.0%) (100 g) was added to a 3 liter separable flask, and then ethylcellosolve acetate (433.3 g) and n-heptane (286.0 g) were added. After stirring for 30 minutes at 20° C., the resulting mixture was left standing and separated. n-Heptane in the recovered lower layer was removed by an evaporator to obtain a novolak resin in ethylcellosolve acetate.

The weight average molecular weight measured by GPC was 9010. The area ratio II was 18.8%.

SYNTHETIC EXAMPLES 38–49

The same procedures as in Synthetic Example 37 were repeated except that the solution of novolak resin in ethylcellosolve acetate in Table 5 was used or the amount of ethylcellosolve acetate solution was changed.

TABLE 5

| Synthetic Example No. | Kind of used resin Synthetic Example No. | The weight average molecular weight converted as polystyrene Mw | The area ratio I | The area ratio II |
| --- | --- | --- | --- | --- |
| 37 | 27 | 9010 | 53.1 | 18.8 |
| 38 | 28 | 11230 | 46.4 | 16.1 |
| 39 | 29 | 12620 | 45.3 | 16.1 |
| 40 | 30 | 8210 | 51.4 | 15.2 |
| 41 | 31 | 9540 | 47.9 | 15.7 |
| 42 | 31 | 7190 | 64.7 | 18.3 |
| 43 | 32 | 11510 | 43.7 | 15.1 |
| 44 | 32 | 9010 | 57.3 | 17.6 |
| 45 | 33 | 9820 | 52.2 | 19.5 |
| 46 | 34 | 11640 | 45.7 | 16.4 |
| 47 | 35 | 12500 | 43.7 | 15.1 |
| 48 | 29 | 16300 | — | 0.9 |
| 49 | 34 | 9150 | — | 18.3 |

EXAMPLES 13–30

Each of the novolak A obtained in Synthetic Example 25, the compound (a) obtained in Synthetic Example 26 and the novolak resins obtained in Synthetic Example 23, 24 and 27–49 was dissolved together with a sensitizer in ethylcellosolve acetate in amounts in Table 6 to prepare a resist solution. The amount of the solvent was adjusted to form a film having a thickness of 1.28 μm when the resist solution was applied under the coating conditions below.

Each composition was filtered through a Teflon (trade mark) filter of 0.2 μm in pore size to prepare a resist solution. The solution was then coated on a silicon wafer, which had been rinsed in a usual manner, by means of a spinner at 4000 rpm. The coated silicon wafer was baked for one minute on a vacuum adsorption-type hot plate kept at 100° C. and exposed to light the exposure time of which was varied stepwise at each shot by means of a reduction projection exposure apparatus with a extra-high pressure mercury lamp as a light source. Thereafter, the silicon wafer was developed in a developer (SOPD (trade name) manufactured by Sumitomo Chemical Company, Limited) to obtain a positive pattern. After rinsing and drying, the amount of film thickness loss for each shot was plotted against the exposure time to calculate sensitivity. The film thickness retention was calculated from the remaining film thickness in the unexposed area. Also, the silicon wafer having a resist pattern was placed for 30 minutes in a clean oven set at various temperatures in the air, and the heat resistance was evaluated by observing the resist pattern by means of a scanning electron microscope.

COMPARATIVE EXAMPLES 5–9

The same procedures as in Example 1 were repeated, except that the novolak A or the compound (a) were not added to prepare a resist composition.

In the same method as in Example 13, the sensitivity and the film thickness retention were calculated and the heat resistance was evaluated.

These results are collectively shown in Table 6.

It is seen from the results in Table 6 that balance between the sensitivity and heat resistance in the Examples is markedly improved in comparison with the Comparative Examples.

TABLE 6

| | Example No. | | | | | | | | | | | |
| --- | --- | --- | --- | --- | --- | --- | --- | --- | --- | --- | --- | --- |
| | 13 | 14 | 15 | 16 | 17 | 18 | 19 | 20 | 21 | 22 | 23 | 24 |
| Amount of the novolak A (parts) | 3.5 | 3.5 | 3.5 | 3.0 | 3.0 | — | — | — | — | — | — | — |
| Amount of the compound (a) (parts) | — | — | — | — | — | 4 | 4 | 4 | 4 | 4 | 3.5 | 4 |
| Kind of novolak resin (Synthetic Example No.) | 37 | 43 | 46 | 44 | 49 | 37 | 38 | 39 | 40 | 41 | 42 | 43 |
| Amount of novolak resin (parts) | 13.5 | 13.5 | 13.5 | 13 | 13 | 13.0 | 13.0 | 13.0 | 13.0 | 13.0 | 13.5 | 13.0 |
| Amount of sensitizer (parts) | 4.5 | 4.5 | 4.0 | 4.5 | 4.0 | 4.0 | 4.0 | 4.0 | 4.0 | 4.0 | 4.0 | 4.0 |
| Kind of Sensitizer | (2) | (2) | (1) | (2) | (2) | (1) | (1) | (1) | (1) | (1) | (1) | (1) |
| Sensitivity (msec) | 128 | 198 | 258 | 187 | 240 | 134 | 164 | 183 | 145 | 189 | 117 | 219 |
| Film thickness retention (%) | 99.5 | 99.7 | 99.9 | 99.8 | 99.9 | 99.6 | 99.6 | 99.5 | 99.8 | 99.5 | 99.7 | 99.8 |
| Heat resistance (°C.) | 160 | 165 | 155 | 160 | 150 | 155 | 160 | 160 | 155 | 155 | 155 | 160 |
| Resolution (μm) | 0.6 | 0.55 | 0.5 | 0.55 | 0.5 | 0.6 | 0.55 | 0.5 | 0.55 | 0.55 | 0.6 | 0.55 |
| Adhesion | ○ | ○ | ○ | ○ | ○ | | | | | | | |

| | Example No. | | | | | | Comp. Ex. No. | | | | |
| --- | --- | --- | --- | --- | --- | --- | --- | --- | --- | --- | --- |
| | 25 | 26 | 27 | 28 | 29 | 30 | 5 | 6 | 7 | 8 | 9 |
| Amount of the novolak A (parts) | — | — | — | — | — | — | — | — | — | — | — |
| Amount of the compound (a) (parts) | 3.5 | 4 | 4 | 4 | 4.5 | 1 | — | — | — | — | 3.5 |
| Kind of novolak resin (Synthetic Example No.) | 44 | 45 | 46 | 47 | 48 | 36 | 34 | 46 | 36 | 40 | 24 |
| Amount of novolak resin (parts) | 13.5 | 13.0 | 13.0 | 13.0 | 12.5 | 16.0 | 17.0 | 17.0 | 17.0 | 17.0 | 13.5 |
| Amount of sensitizer (parts) | 4.0 | 4 | 4 | 4.5 | 4 | 4 | 4.5 | 4.0 | 4 | 4 | 4.5 |

TABLE 6-continued

| Kind of Sensitizer | (1) | (1) | (1) | (2) | (1) | (1) | (2) | (1) | (1) | (1) | (2) |
|---|---|---|---|---|---|---|---|---|---|---|---|
| Sensitivity (msec) | 150 | 214 | 234 | 266 | 246 | 273 | 152 | 1250 | 367 | 780 | 250 |
| Film thickness retention (%) | 99.6 | 100 | 100 | 99.8 | 100 | 99.7 | 98.7 | 100 | 99.7 | 100 | 99.3 |
| Heat resistance (°C.) | 160 | 160 | 165 | 165 | 165 | 155 | 155 | 155 | 155 | 160 | 160 |
| Resolution (μm) | 0.55 | 0.55 | 0.55 | 0.5 | 0.5 | 0.6 | 0.95 | 1.1 | 0.7 | 0.8 | 0.7 |
| Adhesion |  |  |  |  |  |  | Δ | ○ |  |  |  |

SYNTHETIC EXAMPLE 50

Into a three-necked 1000 ml flask, m-methoxyphenol (186 g), 2,3,5-trimethylphenol (136 g), ethylcellosolve acetate (252 g) and a 5% aqueous solution of oxalic acid (30.4 g) were added. Then, to the mixture, a 37.0% formalin (152 g) was dropwise added over 40 minutes while heating and stirring under reflux. Thereafter, the reaction mixture was heated while stirring for further 5 hours. After neutralization, washing with water and removing water, a solution of a novolak resin in ethylcellosolve acetate was obtained.

The weight average molecular weight measured by GPC was 4410.

SYNTHETIC EXAMPLES 51-54

The same procedures as in the Synthetic Example 50 were repeated to obtain resins shown in Table 7.

TABLE 7

| Synthetic Example No. | Molar ratio m-methoxyphenol/ 2,3,5-trimethylphenol | The weight average molecular weight converted to polystyrene Mw | The area ratio II |
|---|---|---|---|
| 50 | 60/40 | 4410 | 22.6 |
| 51 | 60/40 | 6220 | 20.1 |
| 52 | 60/40 | 8660 | 20.8 |
| 53 | 40/60 | 3990 | 21.3 |
| 54 | 40/60 | 4850 | 22.4 |

SYNTHETIC EXAMPLE 55

The solution of novolak resin ethylcellosolve acetate obtained in Synthetic Example 50 (the content of the novolak resin, 40.0%) (100 g) was added to a 3 liter separable flask, and then ethylcellosolve acetate (433.3 g) and n-heptane (286.0 g) were added. After stirring for 30 minutes at 20° C., the resulting mixture was left standing and separated. n-Heptane in the recovered lower layer was removed by an evaporator to obtain a novolak resin in ethylcellosolve acetate.

The weight average molecular weight measured by GPC was 8270. The area ratio II was 7.7%.

SYNTHETIC EXAMPLES 56-61

The same procedures as in Synthetic Example 55 were repeated except that the solution of novolak resin ethylcelosolve acetate in Table 8 was used or the amount of ethylcellosolve acetate solution was changed.

TABLE 8

| Synthetic Example No. | Kind of used resin Synthetic Example No. | The weight average molecular weight converted to polystyrene Mw | The area ratio II |
|---|---|---|---|
| 55 | 50 | 8270 | 7.7 |
| 56 | 50 | 6520 | 10.9 |
| 57 | 51 | 10970 | 8.5 |
| 58 | 51 | 8940 | 9.1 |
| 59 | 52 | 12070 | 9.8 |
| 60 | 53 | 6290 | 12.7 |
| 61 | 54 | 7350 | 11.4 |

EXAMPLES 31-43

Each of the compound (a) obtained in Synthetic Example 26 and the novolak resins obtained in Synthetic Example 23, 24 and 50-61 was dissolved together with a sensitizer in ethylcellosolve acetate in amounts in Table 9 to prepare a resist solution. The amount of the solvent was adjusted to form a film having a thickness of 1.28 μm when the resist solution was applied under the coating conditions below.

Each composition as filtered through a Teflon (Trade mark) filter of 0.2 μm in pore size to prepare a resist solution. The solution was then coated on a silicon wafer, which had been rinsed in a usual manner, by means of a spinner at 4000 rpm. The coated silicon wafer was baked for one minute on a vacuum adsorption-type hot plate kept at 100° C. and exposed to light the exposure time of which was varied stepwise at each shot by means of a reduction projection exposure apparatus with an extra-high pressure mercury lamp as a light source. Thereafter, the silicon wafer was developed in a developing solution (SOPD (trade name) manufactured by Sumitomo Chemical Company, Limited) to obtain a positive pattern. After rinsing and drying, the amount of film thickness loss for each shot was plotted against the exposure time to calculate sensitivity. The film thickness retention was calculated from the remaining film thickness in the unexposed area. Also, the silicon wafer having a resist pattern was placed for 30 minutes in a clean oven set at various temperatures in the air, and the heat resistance was scanning electron microscope.

COMPARATIVE EXAMPLES 10-11

The same procedures as in Example 31 were repeated, except that the compound (a) was not added to prepare a resist composition.

In the same method as in Example 31, the sensitivity and the film thickness retention were calculated and the heat resistance was evaluated.

These results are collectively shown in Table 9.

It is seen from the results in Table 9 that valance between the sensitivity and heat resistance in the Examples is markedly improved in comparison with the Comparative Examples.

TABLE 9

| | Example No. | | | | | | | | | | | | | Comp. Ex. No. | |
|---|---|---|---|---|---|---|---|---|---|---|---|---|---|---|---|
| | 31 | 32 | 33 | 34 | 35 | 36 | 37 | 38 | 39 | 40 | 41 | 42 | 43 | 10 | 11 |
| Amount of the compound (a) (parts) | — | — | — | — | — | 3.5 | 4 | 3.5 | 4 | 3.5 | 3.5 | 3.5 | 3.5 | — | — |
| Kind of novolak resin (Synthetic Example No.) | 50 | 51 | 52 | 53 | 54 | 53 | 55 | 56 | 57 | 58 | 59 | 60 | 61 | 23 | 61 |
| Amount of novolak resin (parts) | 17 | 17 | 17 | 17 | 17 | 13.5 | 13 | 13.5 | 13 | 13.5 | 13.5 | 13.5 | 13.5 | 17 | 17 |
| Sensitizer: | | | | | | | | | | | | | | | |
| Kind | (1) | (1) | (1) | (2) | (2) | (1) | (1) | (1) | (2) | (1) | (2) | (2) | (2) | (1) | (2) |
| Amount (parts) | 4 | 4 | 4 | 4.5 | 4.5 | 4 | 4 | 4 | 4.5 | 4 | 4.5 | 4.5 | 4.5 | 4 | 4.5 |
| Sensitivity (msec) | 251 | 294 | 358 | 227 | 284 | 253 | 213 | 178 | 172 | 257 | 205 | 253 | 287 | 285 | 970 |
| Film thickness retention (%) | 99.1 | 99.2 | 99.4 | 98.8 | 99.0 | 99.7 | 99.7 | 99.5 | 99.1 | 99.5 | 99.1 | 99.3 | 99.3 | 98.7 | 99.8 |
| Heat resistance (°C.) | 150 | 155 | 160 | 165 | 165 | 155 | 160 | 160 | 160 | 165 | 165 | 165 | 165 | 140 | 160 |
| Resolution (μm) | 0.55 | 0.6 | 0.65 | 0.6 | 0.65 | 0.55 | 0.55 | 0.55 | 0.6 | 0.55 | 0.6 | 0.6 | 0.6 | 0.8 | 0.8 |

What is claimed is:

1. A positive resist composition comprising an admixture of a 1,2-quinonediazide compound, an alkali-soluble resin (I) obtainable through a condensation reaction of a mixture of m-cresol, 2,3,5-trimethylphenol and optionally p-cresol with an aldehyde selected from the group consisting of formaldehyde, paraformaldehyde, acetaldehyde and glyoxal, and a compound of the general formula (III):

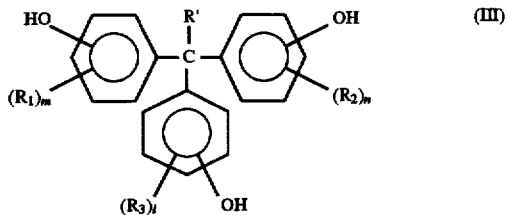

wherein $R_1$, $R_2$ and $R_3$ are respectively a $C_1$–$C_5$ alkyl group or a $C_1$–$C_5$ alkoxy group; l and n are each 2, and m is zero; and R' is a hydrogen atom or a $C_1$–$C_3$ alkyl group and wherein said compound of formula (III) is obtainable through a condensation reaction of a phenol compound with a carbonyl compound selected from the group consisting of o-hydroxybenzaldehyde, m-hydroxybenzaldehyde, p-hydroxybenzaldehyde and 3-methoxy-4-hydroxybenzaldehyde in the presence of an acid catalyst.

* * * * *